US012730114B2

(12) United States Patent
De Luca

(10) Patent No.: US 12,730,114 B2
(45) Date of Patent: Sep. 8, 2026

(54) METHOD FOR CLASSIFYING AN ALLERGIC PATIENT AS ELIGIBLE TO ALLERGEN IMMUNOTHERAPY

(71) Applicant: Stallergenes Greer International AG, Baar (CH)

(72) Inventor: Giampiero De Luca, Geneva (CH)

(73) Assignee: Stallergenes Greer International AG, Baar (CH)

( * ) Notice: Subject to any disclaimer, the term of this patent is extended or adjusted under 35 U.S.C. 154(b) by 1075 days.

(21) Appl. No.: 17/554,179

(22) Filed: Dec. 17, 2021

(65) Prior Publication Data

US 2022/0196675 A1 Jun. 23, 2022

(30) Foreign Application Priority Data

Dec. 18, 2020 (EP) .................................... 20215377

(51) Int. Cl.
*A61K 39/35* (2006.01)
*C12N 5/078* (2010.01)
*G01N 33/68* (2006.01)

(52) U.S. Cl.
CPC ......... *G01N 33/6869* (2013.01); *A61K 39/35* (2013.01); *C12N 5/0634* (2013.01); *G01N 2333/5406* (2013.01); *G01N 2333/5437* (2013.01); *G01N 2800/52* (2013.01)

(58) Field of Classification Search
CPC ....... G01N 33/6869; G01N 2333/5406; G01N 2333/5437; G01N 2800/52; G01N 2333/54; G01N 2333/5409; G01N 2333/5425; A61K 39/35; C12N 5/0634
See application file for complete search history.

(56) References Cited

U.S. PATENT DOCUMENTS 6,120,769 A * 9/2000 Gefter ................ G01N 33/5091 435/7.1

FOREIGN PATENT DOCUMENTS

| | | |
|---|---|---|
| EP | 2948770 | 12/2015 |
| EP | 3 418 738 | 12/2018 |
| EP | 2 948 770 B1 | 11/2020 |
| WO | 2012/137180 A2 | 10/2012 |
| WO | 2014/115102 A1 | 7/2014 |
| WO | 2016/079339 A1 | 5/2016 |
| WO | 2017/121883 A1 | 7/2017 |
| WO | 2019/211312 A1 | 11/2019 |

OTHER PUBLICATIONS

Woodfolk JA. T-cell responses to allergens. J Allergy Clin Immunol. 2007;119(2):280-296. (Year: 2007).*

(Continued)

*Primary Examiner* — Joanne Hama
*Assistant Examiner* — Hannah Sunshine
(74) *Attorney, Agent, or Firm* — Morgan, Lewis & Bockius LLP

(57) ABSTRACT

Disclosed is a method of improving global response to allergen desensitization, by allergen immunotherapy, which includes classifying allergic patients as eligible to allergen immunotherapy based on the patients' allergen-specific T cell reactivity against the allergen.

18 Claims, 1 Drawing Sheet

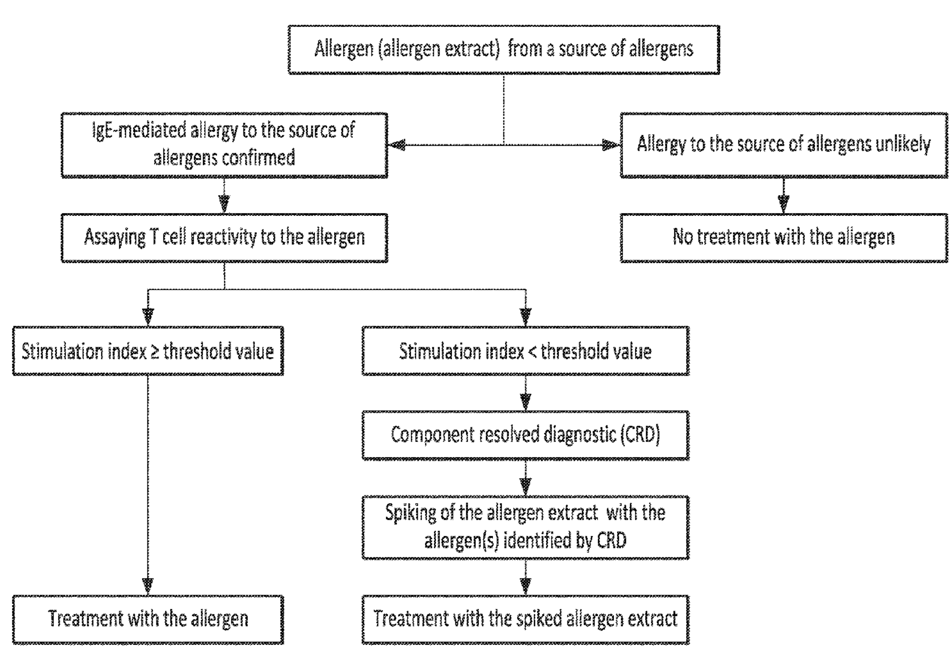

(56) References Cited

OTHER PUBLICATIONS

Schenk S, Breiteneder H, Susani M, et al. T-cell epitopes of Phl p 1, major pollen allergen of timothy grass (*Phleum pratense*): evidence for crossreacting and non-crossreacting T-cell epitopes within grass group I allergens. J Allergy Clin Immunol. 1995;96(6 Pt 1):986-996. (Year: 1995).*
Platts-Mills T, Vaughan J, Squillace S, Woodfolk J, Sporik R. Sensitisation, asthma, and a modified Th2 response in children exposed to cat allergen: a population-based cross-sectional study. Lancet. 2001;357(9258):752-756. (Year: 2001).*
Pene J, Desroches A, Paradis L, et al. Immunotherapy with Fel d 1 peptides decreases IL-4 release by peripheral blood T cells of patients allergic to cats. J Allergy Clin Immunol. 1998;102(4 Pt 1):571-578. (Year: 1998).*
Daigle BJ, Rekkerth DJ. Practical recommendations for mixing allergy immunotherapy extracts. Allergy Rhinol (Providence). 2015;6 (1):1-7 (Year: 2015).*
Huss-Marp J, Raulf M, Jakob T. Spiking with recombinant allergens to improve allergen extracts: benefits and limitations for the use in routine diagnostics: Part 19 of the Series Molecular Allergology. Allergo J Int. 2015;24:236-243 (Year: 2015).*
Zhernov Y, Curin M, Khaitov M, Karaulov A, Valenta R. Recombinant allergens for immunotherapy: state of the art. Curr Opin Allergy Clin Immunol. 2019;19(4):402-414 (Year: 2019).*
Matricardi PM, Kleine-Tebbe J, Hoffmann HJ, et al. EAACI Molecular Allergology User's Guide. Pediatr Allergy Immunol. 2016;27 Suppl 23:1-250. (Year: 2016).*
Clark et al., "Assessment of combined symptom and medication scores for rhinoconjunctivitis immunotherapy clinical trials", Allergy 2007, 2007, vol. 62, pp. 10239-1028.
Curin et al., "How Allergen Extracts are Made-From Source Materials to Allergen Extracts; Single recombinant and purified major allergens and peptides; How they are made and how they change allergy diagnosis and treatment", Ann Allergy Asthma Immunol, 2017, vol. 119, pp. 201-209.
Hauser et al., "Panallergens and their impact on the allergic patient", Allergy, Asthma & Clinical Immunology, 2010, vol. 6, No. 1, pp. 1-14.
Larsen et al., "Allergen nomenclature", The Journal of Allergy and Clinical Immunology, Feb. 1996, vol. 97, No. 2, pp. 577-578.
Pfaar et al., "Recommendations for the standardization of clinical outcomes used in allergen immunotherapy trials for allergic rhinoconjunctivitis: an EAACI Position Paper", Allergy, 2014, vol. 69, pp. 854-867.
Pomés et al., "WHO/IUIS Allergen Nomenclature: Providing a common language", Molecular Immunology, 2018, vol. 100, pp. 3-13.
Schulten, "Strategies to Study T Cells and T Cell Targets in Allergic Disease", Allergen, 2017, Chapter 7, pp. 123-138.
Senna et al., "An evidence-based appraisal of the surrogate markers of efficacy of allergen immunotherapy", Current Opinion in Allergy and Clinical Immunology, 2011, vol. 11, No. 4, pp. 375-380.
Shamji et al., "Predictive biomarkers of clinical efficacy of allergen-specific immunotherapy: how to proceed", Immunotherapy, 2013, vol. 5, No. 3, pp. 203-206.
Tscheppe et al., "Development of a novel Ara h 2 hypoallergen with no IgE binding or anaphylactogenic activity", Journal of Allergy and Clinical Immunology, Jan. 2020, vol. 145, pp. 229-238.
Valenta et al., "The recombinant allergen-based concept of componentresolved diagnostics and immunotherapy (CRD and CRIT)", Clinical and Experimental Allergy, 1999, vol. 29, pp. 896-904.
Wambre et al., "Characterization of CD4+ T cell subsets in allergy", Current Opinion in Immunology, 2012, vol. 24, pp. 700-706.
Search Report for EP20215377, dated May 31, 2021, 3 pages.
Mueller et al., "Allergen immunotherapy in people, dogs, cats and horses—differences, similarities and research needs" , Allergy, May 27, 2018, 11 pages.
Schulten et al., "Previously undescribed grass pollen antigens are the major inducers of T helper 2 cytokine-producing T cells in allergic individuals", Proceedings of the National Academy Of Sciences, vol. 110, No. 9, Feb. 26, 2013, pp. 3459-3464.
Benjaponpitak et al., "The kinetics of change in cytokine production by CD4+ T cells during conventional allergen immunotherapy", Journal of Allergy and Clinical Immunology, vol. 103, No. 3, Mar. 1, 1999, pp. 468-475.
Schulten et al., Association between specific timothy grass antigens and changes in THI- and TH2-cell responses following specific immunotherapy, Journal of Allergy and Clinical Immunology, vol. 134, No. 5, Nov. 1, 2014, pp. 1076-1083.
Akdis et al., "Type 2 immunity in the skin and lungs", Allergy, 2020, vol. 75. pp. 1582-1605.
Jutel et al., "Bee Venom Immunotherapy Results in Decrease of IL-4 and IL-5 and Increase of IFN-gamma Secretion in Specific Allergen-Stimulated T Cell Cultures", The American Association of Immunologists, downloaded May 28, 2021, 8 pages.

* cited by examiner

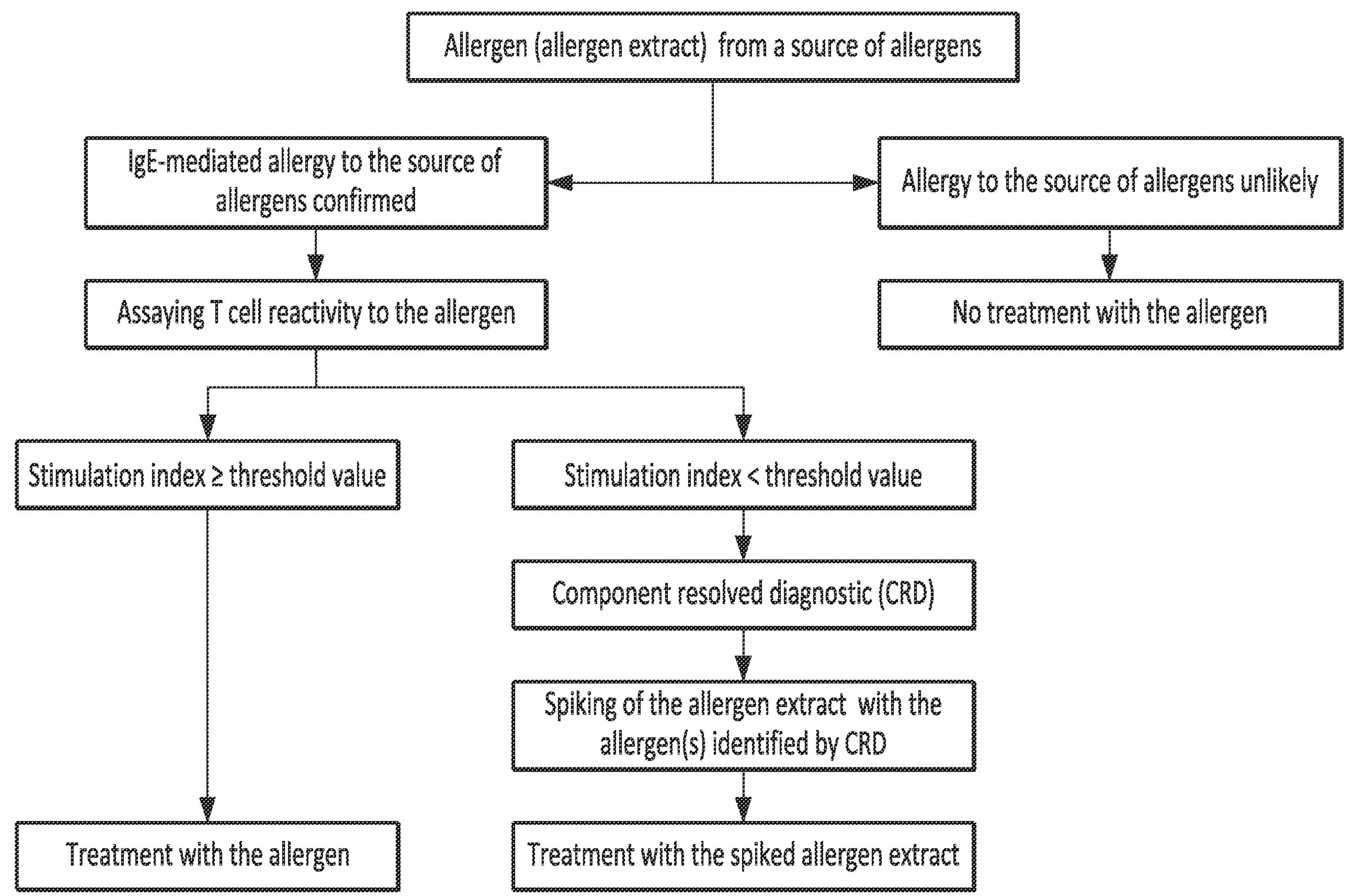
Allergen (allergen extract) from a source of allergens
IgE-mediated allergy to the source of allergens confirmed
Allergy to the source of allergens unlikely
Assaying T cell reactivity to the allergen
No treatment with the allergen
Stimulation index ≥ threshold value
Stimulation index < threshold value
Component resolved diagnostic (CRD)
Spiking of the allergen extract with the allergen(s) identified by CRD
Treatment with the allergen
Treatment with the spiked allergen extract

METHOD FOR CLASSIFYING AN ALLERGIC PATIENT AS ELIGIBLE TO ALLERGEN IMMUNOTHERAPY

CROSS-REFERENCE TO RELATED APPLICATIONS

This application claims the benefit of EP patent application No. 20215377.1, filed Dec. 18, 2020, the entire contents of which is hereby incorporated herein by reference.

BACKGROUND OF THE INVENTION

Field of the Invention

The present invention concerns a method of improving global response to allergen desensitization, by allergen immunotherapy, which comprises classifying allergic patients as eligible to allergen immunotherapy based on the patients' allergen-specific T cell reactivity against the allergen.

Description of the Related Art

Allergy is a major and growing health concern around the world. As societies become more affluent and reduce the incidence of contagious disease, the prevalence of allergic disease increases. Finding effective treatments for allergy, both preventive and therapeutic, is a growing challenge for today's healthcare industry. Traditionally, management of allergy has concentrated on alleviation of symptoms, using antihistamines and medications that relieve allergic symptoms including nasal congestion, dermatitis and asthma, such as decongestants, creams, anti-inflammatories and bronchodilators. Allergen avoidance is another strategy for allergy management, but this is often difficult or impossible, particularly in the case of pervasive allergens such as pollen. A third alternative is specific allergy vaccination, or allergen immunotherapy (AIT), in which patients are inoculated with the allergen causing the allergy in order to obtain an improvement in the patient's immune status. This kind of treatment has the advantage of altering the course of the illness to prevent the manifestation of symptoms, rather than simply alleviating symptoms.

Injective immunotherapy (subcutaneous immunotherapy or SCIT) was first reported in 1911 and has been used in clinical practice since the 1970s. However, the invasive nature of the therapy, requiring regular clinician visits, and problems with side effects—including in rare cases anaphylaxis and death—have impacted its uptake as a treatment of allergy. Immunotherapy via administration of allergen to mucosa, such as the oral mucosa of the mouth and gut, has also been explored. Sublingual immunotherapy (SLIT), in which vaccine is administered underneath the tongue and absorbed via the sublingual mucosa, is a well-established alternative to injective immunotherapy. SLIT has been shown to be comparable to SCIT in terms of efficacy and has a superior safety profile. It is now generally preferred to SCIT due to the less invasive nature to the technique and the lower risk of side effects, as the occurrence of harmful side effects from SLIT is relatively low. However, the expense of the treatment is still a major factor in slowing down the uptake of SLIT.

Patients' eligibility to AIT is currently based on anamnesis and the determination of IgE reactivity to a specific allergen by skin prick or in vitro testing. However, patient selection would greatly benefit from the identification of biomarkers predicting the likelihood of clinical improvement following AIT (Senna et al. Curr Opin Allergy Clin Immunol 11, 375-380 (2011); Shamji, et al. Immunotherapy 5, 203-206 (2013)).

The international patent application WO 2012/137180 has described that Fetuin-A, beta-2 glycoprotein 1, Antithrombin-III, MCP-1 and Eotaxin constitute predictive biomarkers of responsiveness of a patient to allergen immunotherapy. The international patent application WO2016079339 has more specifically disclosed that a certain form of sialylated Fetuin-A is predictive of responsiveness of a patient to allergen immunotherapy. Furthermore, the international patent application WO2017121883 has described that IL-10 expression before initiation of AIT is predictive of responsiveness of house dust mite allergic patients to AIT.

However, there is a need for a global method for selecting patients for allergen immunotherapy in order to improve response to allergen desensitization, in particular for pollen and/or food allergens.

Type I allergy is an immunoglobulin E (IgE)-mediated chronic disease. As such, disease diagnosis and identification of targeted allergens are primarily based on specific IgE reactivity. However, immunological studies have shown that T cells play a key role early on, before allergic disease is even established. Susceptible individuals initially exposed to allergen mount a dominant Th2 response, resulting in the production of type 2 cytokines, such as IL-4 and IL-13. These cytokines along with a direct physical interaction of T and B cells provide the signal for B cells to undergo antibody class switching and produce allergen-specific IgE, thereby leading to allergen sensitization. While IgE mediate immediate-type allergic reactions occurring within minutes of exposure to the allergen, allergen-specific Th2 cells mediate late-phase reactions and promote inflammation (Schulten V., 2017, Strategies to Study T Cells and T Cell Targets in Allergic Disease, in Allergen, IntechOpen, Edited by Seyyed Shamsadin Athari, DOI: 10.5772/intechopen.68923).

In particular, Th2 cytokines inhibit the differentiation and induction of IL-10-secreting Tr1 cells and IFN-g secreting Th1 cells. It has been proposed that high allergen dose during the course of AIT induces apoptosis of CD27- allergen-specific Th2 cells which are typically in the final stages of differentiation. In contrast, the less differentiated $CD27^+$ allergen-specific Th1/Tr1 cells are more resistant to apoptosis. Hence, the latter would become increasingly dominant. Stimulation of Th1/Tr1 cells leads to IFN-γ and IL-10 production and the induction of allergen specific IgG4 and IgA that can suppress the Type 1 allergic immune response (Wambre et al. Curr Opin Immunol. 2012 December; 24 (6): 700-706.).

Currently, allergen extracts containing mixtures of allergens and non-allergenic proteins are used for immunotherapy.

Allergen-specific immunotherapy with whole extract can be associated with IgE-mediated adverse reactions that result from the patient's allergen-specific IgE molecules being cross-linked by the allergen present in the extract used for treatment, triggering degranulation and immediate-type reactions. For this reason, researchers have strived to find a treatment that targets T cells and circumvents potential IgE reactivity. Removal of IgE epitopes, thereby eliminating the risk of IgE cross-linking, is one obvious approach (Schulten V., 2017, supra).

Allergenic pollens and allergenic foods contain complex mixtures of several molecules including major and minor allergens. Major allergens represent components to which the majority of patients (by definition >50%) reacting to a given allergen source is sensitized (IgE reactivity), whereas minor allergens are recognized by a more limited number of patients (<50%) (Larsen J N, Lowenstein H.Allergen nomenclature. J Allergy Clin Immunol 1996; 97:577-8).

However, standardization of allergenic extracts relies on the use of company-specific allergenic units that are usually based on the concentration of the main IgE-binding molecule in the allergen extract. Therefore, such extracts might not be adequate for treating patients reacting to minor allergens. Indeed, allergen extracts have variable content of major and minor allergens, as they are subject to batch to batch variation and sometimes important allergens are even not present in the extracts (Curin et al., Ann Allergy Asthma Immunol 119 (2017) 201e209). In addition, relevant allergens, especially minor allergens, for a given patient might be underrepresented or even missing in the extract used for therapy (Hauser et al., Allergy, Asthma & Clinical Immunology 2010, 6:1). It has been suggested that this problem could be circumvented by molecule-based diagnostics and custom-tailored immunotherapy using a panel of naturally purified or recombinantly produced allergens (Valenta et al., Clin Exp Allergy 1999, 29:896-904; Hauser et al., Allergy, Asthma & Clinical Immunology 2010, 6:1; Curin et al., Ann Allergy Asthma Immunol 119 (2017) 201e209). Yet, as of today, no highly purified or recombinant allergen has been authorized for marketing in Europe or North America.

Component resolved diagnosis (CRD) is based on the determination of specific IgE concentration against individual allergenic proteins. CRD can discriminate genuine sensitization from cross-reactivity. This information may be valuable when deciding about immunotherapy, the rationale of the approach being to select for allergen-specific immunotherapy (AIT) with allergen extracts those patients sensitized to the main allergen of the allergen extract (Valenta et al., Clin Exp Allergy 1999, 29:896-904).

Yet, while it is commonly admitted that suitability of a modified allergen, with no IgE binding or anaphylactogenic activity, for AIT requires retaining T-cell activation (see for instance Tscheppe et al. J Allergy Clin Immunol 2020; 145:229-38), it has never been suggested that eligibility of an allergic patient for ongoing allergen immunotherapy should conversely requires that the T cells of the patient be activated by the allergen used in immunotherapy.

BRIEF SUMMARY OF THE INVENTION

The invention aims at selecting patients who are more likely to respond to a specific allergen immunotherapy. It is assumed that efficacy of allergen immunotherapy is globally affected by a "dilution effect" that results from treating a population of patient having similar symptoms but resulting from different allergens although belonging to the same family or allergen source. For instance, for patients having allergy to birch pollen, some may be allergic to the major allergen Bet v 1 and with or without reactivity to minor allergens such as Bet v 2 and Bet v4, while some may be allergic to one or more minor allergens but no to the major allergen Bet v 1. However, all those patients are currently treated with a same birch pollen extract, in which—subject to batch to batch variation—an given allergen will be more or less represented, or even missing. Efficacy of allergen immunotherapy is therefore likely to be uneven depending on the allergenic profile of the patients. Yet, no solution has been proposed so far to address this issue.

BRIEF DESCRIPTION OF THE SEVERAL VIEW OF THE DRAWING(S)

FIG. 1 is an illustration of the rationale of the method of classifying patients according to the invention.

DETAILED DESCRIPTION OF THE INVENTION

The invention thus relates to a method for classifying an allergic patient as eligible to allergen immunotherapy, said method comprising screening the T cell reactivity of said patient to an allergen, said screening comprising the following steps:

a) contacting with an allergen an isolated biological sample of the patient containing T cells,
b) measuring T cell reactivity to said allergen,
c) calculating a stimulation index as the ratio of the T cell reactivity measured in step b) on T cell reactivity of the isolated biological sample of the patient containing T cells unstimulated by the allergen, and
d) classifying said patient as being eligible to treatment with a composition comprising said allergen if stimulation index is equal or above a threshold value.

According to the method for classifying an allergic patient, if the calculated stimulation index is below the threshold value, the allergic patient is classified as not eligible to treatment with a composition comprising said allergen.

According to an embodiment, the method further comprises administering to the patient a composition comprising the allergen if the patient is classified as being eligible to treatment with a composition comprising said allergen.

According to another embodiment, the method further comprises, if the patient is not classified as eligible to treatment with a composition comprising said allergen:

e) Determining the patient's sensitivity to individual allergenic proteins of the allergen;
f) Spiking the allergen with the allergenic protein(s) to which the patient is sensitized; and
g) Administering to the patient the spiked allergen.

The invention also relates to an allergen for use in a method of allergen immunotherapy, wherein said method comprises identifying if an allergic patient is eligible to treatment with a composition comprising the allergen by the method of the invention, and administering to the patient a composition comprising the allergen if the patient is identified as eligible to treatment with said composition comprising the allergen.

The invention further relates to a spiked allergen for use in a method of allergen immunotherapy, wherein said method comprises classifying an allergic patient as not eligible to treatment with a composition comprising the allergen by a method of the invention, determining the patient's sensitivity to individual allergenic proteins of the allergen, spiking the allergen with the allergenic protein(s) to which the patient is sensitized, and administering to the patient a composition comprising the spiked allergen.

Immunotherapy

"Allergen Immunotherapy" is intended to mean a treatment of allergy by inducing, enhancing, or suppressing an immune response by administration of one or more allergens.

"Therapy", "therapeutic", "treatment" or "treating" include reducing, alleviating or inhibiting or eliminating the causes of a disease or pathological conditions (e.g. allergy), as well as treatment intended to reduce, alleviate, inhibit or eliminate symptoms of said disease or pathological condition. These terms may include preventive treatment which is intended to, or has the effect of preventing onset of the disease or pathological condition, or reducing, alleviating, inhibiting or eliminating future symptoms. They may also include treatment of ongoing symptoms.

"Allergy", or "type 1 hypersensitivity", is a condition characterized by production of allergen-specific IgE in response to a specific allergen, usually a protein. Clinical manifestations and symptoms of allergy may include nasal congestion, nasal pruritis, ocular pruritis, tearing, rhinorrhoea, sinusitis, rhinitis, sneezing, wheezing, conjunctivitis, dermal itching, dermatitis, skin irritation, hives, shortness of breath, repetitive cough and asthma.

In relation to allergy, immunotherapy comprises administering an allergen to the patient in order to treat allergy to the allergen of the patient, i.e. reducing current or future immune response, such as an allergen-specific IgE response and/or histamine release by mastocytes and/or granulocytes induced by the allergen, and/or manifestation of clinical symptoms of allergy. Immunotherapy is conventionally carried out by administering repeatedly a monodose or incremental doses of an allergen to a patient in need thereof, thereby resulting in an adaptive immune response of the patient who becomes desensitised to the allergen.

In some embodiments, allergen immunotherapy comprises administration of a composition comprising the allergen to a mucosal surface, such as a sublingual, oral, nasal, buccal, ocular, rectal, vaginal, pulmonary or ear surface. In particular, immunotherapy is preferably sublingual immunotherapy. Alternatively, in other embodiments immunotherapy comprises administration via a parenteral route, such as intralymphatic, subcutaneously or intravenously, for example via injection, or via alternative routes such skin immunisation e.g. transdermal or epicutaneous administration. In particular, "epicutaneous administration" refers to the application of an allergen on the skin of the subject under conditions allowing a contact with the surface of the skin. Skin application is preferably performed without any skin perforation or pretreatment. Skin application is preferably maintained in conditions allowing penetration of the allergen in the superficial layer(s) of the skin and/or and for a period of time sufficient to allow contact of the allergen with immune cells.

An allergen is a substance, usually a protein, which elicits the production of IgE antibodies in predisposed individuals.

The "allergen" used for immunotherapy comprises an allergen extract (including mixture of allergen extracts) or a mixture of allergenic peptides. Accordingly, the allergen immunotherapy comprises administering a composition comprising an allergen extract or a mixture of allergenic peptides to the patient.

An allergen extract is prepared by extraction from its natural source material, usually by aqueous extraction and one or more purification steps, and yield aqueous extract which is a complex mixture of allergenic proteins. The allergen extract may be native (i.e. not modified) or modified to reduce IgE reactivity, such as an allergoid (chemically modified form of a native occurring allergen extract which has been chemically modified for example by aldehydation).

Allergenic peptides are typically prepared by denaturation and hydrolyzation of a purified allergen extract to produce allergen fragments. An exemplary method of preparing allergenic peptides is disclosed in the international patent application WO 2019/211312. Allergenic peptides are associated with reduced allergenicity and consequently reduced risk of systemic reaction as compared to the non-hydrolyzed allergen.

The composition comprising the allergen used for immunotherapy may be in liquid phase, solid phase or a combination of both such as adsorbed vaccine. For epicutaneous administration, the composition comprising the allergen is preferably included in a skin device, such as a patch.

The allergen may include pollen allergens (such as tree, herb, weed and grass pollen allergens), insect allergens (such as inhalant, saliva and venom allergens, e.g. cockroach, midge and house dust mite allergens and Hymenoptera venom allergens), animal hair and dander allergens (from e.g. dog, cat, horse, rat, mouse, rabbit) and food allergen. Food allergens may derive from milk, eggs, vegetables (including peanut and soybean), nuts and hazelnuts, wheat, crustaceans, fish and shellfish and derivative products thereof. In particular, food allergens may be ovalbumin or gluten.

Important pollen allergens from trees, grasses and herbs are such originating from the taxonomic orders of Fagales, Oleales, Pinales and platanaceae including e.g. birch (*Betula*), alder (*Alnus*), hazel (*Corylus*), hornbeam (*Carpinus*) and olive (*Olea*), cedar (*Cryptomeria* and *Juniperus*), Plane tree (*Platanus*), the order of Poales including e.g. grasses of the genera *Lolium, Phleum, Poa, Cynodon, Dactylis, Holcus, Phalaris, Secale*, and Sorghum, the orders of Asterales and Urticales including e.g. herbs of the genera *Ambrosia, Artemisia*, and *Parietaria*. Other important inhalation allergens are those from house dust mites of the genus *Dermatophagoides* and Euroglyphus, storage mite e.g *Lepidoglyphys, Glycyphagus* and *Tyrophagus*, those from cockroaches, midges and fleas e.g. *Blatella, Periplaneta, Chironomus* and *Ctenocepphalides*, and those from mammals such as cat, dog and horse, venom allergens including such originating from stinging or biting insects such as those from the taxonomic order of Hymenoptera including bees (superfamily Apidae), wasps (superfamily Vespidea), and ants (superfamily Formicoidae). Important inhalation allergens from fungi are e.g. such originating from the genera *Alternaria* and *Cladosporium*.

Examples of various known protein allergens derived from some of the above-identified sources include: *Betula* (*verrucosa*) Bet v 1, Bet v 2, Bet v 3, Bet v 4, Bet v 5, Bet v 6, Bet v 7, Bet v 8; Blomia (*tropicalis*) Blo t 1, Blo t 2, Blo t 3, Blo t 4, Blo t 5, Blo t 6, Blo t 7, Blo t 8, Blot 10, Blo t 11, Blot 12, Blo t 13, Blo t 19, Blo t 21; *Cynodon* (*dactylon*) Cyn d 1, Cyn d 7, Cyn d 12, Cyn d 15, Cyn d 22, Cyn d 23, Cyn d 24; *Dermatophagoides* (*pteronyssinus* or *farinae*) Der p 1, Der p 2, Der p 3, Der p 4, Der p 5, Der p 6, Der p 7, Der p 8, Der p 9, and other Der p allergens; Der f 1 Der f2, Der f 3, Der f4, Der f 5, Der f 6, Der f 7, Der f 8 and other Der f allergens; *Felis* (*domesticus*) Fel d 1, Fel d 2, Fel d 3, Fel d4, Fel d 5, Fel d 6, Fel d 7, and Fel d 8; *Ambrosia* (*artemiisfolia*) Amb a 1, Amb a 2, Amb a 3, Amb a 4, Amb a 5, Amb a 6, Amb a 7, Amb a 8, Amb a 9, Amb a 10, Amb a 11, and Amb a 12; *Lolium* (*perenne*) Lol p 1, Lol p2, Lol p 3, Lol p 4, Lol p5 and Lol p 11; *Cryptomeria* (*japonica*) Cry j 1, Cry j 2, Cry j 7; *Canis* (*familiaris*) Can f 1, Can 12, Can f 3, Can f4, Can f5, Can f6, Can f7, and Can f8; *Juniperus* (*sabinoides* or *virginiana*) Jun s 1; Jun v 1. Jun v 3; *Juniperus* (*ashei*) Jun a 1; Jun a 2, Jun a 3, and Jun a 7; *Dactylis* (*glomerata*) Dac g 1, Dac g 2, Dac g3, Dac g 4 and Dac g 5; Poa (*pratensis*) Poa p 1, and Poa p 2; *Phleum* (pretense) Phi p 1, Phi p2, Phi p 3, Phi p 4, Phi p 5, Phi p 6, Phi p 7, Phi p 11, Phi p 12 and Phi p 13; and Sorghum (*halepense*) Sor h 1, Sor h 2 and Sor h 3.

Furthermore, the designation of an allergen actually encompasses one or more isoallergens or variants (isoforms) from the same source that are defined based on their amino acid sequence identity and IgE cross-reactivity (Pomes et al., Molecular Immunology 100 (2018) 3-13). Accordingly, an allergen extract from one of the above sources comprises a mixture of all or part of the corresponding allergen proteins.

According to an embodiment, the allergen immunotherapy comprises administering a composition comprising an allergen extract or mixture of allergenic peptides from pollen (from tree, herb, weed or grass), from food, from a house dust mite, or from an animal or insect.

An allergen extract may comprise for instance a total amount of 0.01-10,000 μg, preferably 0.01-1000 μg, preferably 0.1-500 μg of allergens, more particularly of major allergens.

The allergen content of the composition may be expressed in term of biopotency (allergenic activity as measured in vivo and/or in vitro) for which there is currently no internationally accepted standardised method. The bio-potency of a given extract mostly depends on the content of relevant allergens in the extract, which content varies with the biological source material. Different units have been developed such as IR (index of reactivity), BAU (Bioequivalent Allergen Units), AU (Allergy Units), SQ-Units (Standardised Quality Units). Index of Reactivity or IR are established on the basis of Stallergenes' biopotency IR standardised method. The IR can be determined by means of an immunoassay such as inhibition ELISA assay. 100 IR containing grass pollen extracts equal around 3000 BAU. BAU or Bioequivalent Allergen Units is the biopotency units established on the basis of the FDA requirements described in "Methods of the Allergenics Products Testing Laboratory", October 1993. As to its potency, the composition used for immunotherapy may comprise for instance a total value of 0.01-10,000 IR, preferably 0.1-1,000 IR, preferably 1-500 IR, preferably 100-300 IR.

An allergic patient is classified as eligible to allergen immunotherapy if it is expected that the patient will show a response to allergen immunotherapy, or be responder to allergen immunotherapy. An allergic patient is classified as not eligible to allergen immunotherapy if it is expected that the patient will not show a response to allergen immunotherapy, or will be non-responder to allergen immunotherapy.

"Response" of a patient to treatment indicates that the patient manifests a reduction in the clinical symptoms. Clinical symptoms may be assessed over the course of treatment, i.e. symptoms before treatment may be compared to symptoms during and after treatment. Alternatively, a reduction in symptoms may be determined by comparison to a baseline level established before treatment. Concerning allergy, this approach is particularly useful where, for example, immunotherapy is carried out in patients not currently experiencing symptoms, as may be the case for seasonal grass pollen allergy sufferers, who may be treated before the pollen season. Symptoms may be assessed by standard methods, such as patient self-assessment or record of the amount of medication required. The degree of a patient's response to treatment may be assessed by measuring the degree of reduction of severity in symptoms.

A "responder" subject as defined herein is a subject who responds to immunotherapy or vaccine administration with an improvement in clinical symptoms, preferably a statistically significant improvement as compared to patients receiving placebo or no treatment. Preferably, a responder subject will demonstrate at least 10%, 11%, 12%, 13%, 14%, 15%, 16%, 17%, 18%, 19%, 20%, 25%, 30%, 35% or 50% improvements of clinical symptoms. As another preferred embodiment, a responder subject will demonstrate an improvement in clinical symptoms which is greater than the average or median improvement seen in a random sample of subjects.

A "non-responder" subject is a subject who does not manifest any improvement in clinical symptoms following immunotherapy or vaccine administration, or who demonstrates a non-statistically significant improvement in symptoms, or who demonstrate less than 10%, 11%, 12%, 13%, 14%, 15%, 16%, 17%, 18%, 19%, 20%, 25%, 30%, 35% or 50% improvement of clinical symptoms, or who demonstrates an improvement in clinical symptoms which is less than the average or median improvement seen in a random sample of subjects.

For example, improvement in clinical symptoms for type 1 hypersensitivity or allergy may be detected by:

- a reduction in the frequency or severity of nasal congestion, nasal pruritis, ocular pruritis, tearing, rhinorrhoea, sinusitis, rhinitis, sneezing, wheezing, conjunctivitis, dermal itching, dermatitis, skin irritation, hives, shortness of breath, repetitive cough and asthma, and/or
- reduction in the uptake of known relief medication such as anti-histaminic, corticosteroids, bronchodilatator agents or antileukotriene agents.
- An improvement of a lung function test such as air flow debit, flow volume, FEV1 (forced expiratory volume in 1 second),
- A reduction in inflammatory parameters such as NO
- A reduction in the reactivity to an allergen challenge such as, intranasal, intraconjunctivial, Intrabronchial, skin prick test Moreover, improvement of clinical symptoms may also be demonstrated on the basis of a combination thereof such as Symptoms Score (e.g. Rhinoconjunctivitis Total Symptom Score (RTSS) or Average Rhinoconjunctivitis Total Symptom Score (ARTSS)), Medication Score (e.g. Rescue Medication Score (RMS) or Average Rescue Medication Score (ARMS)), Combined Scores (e.g. Combined Symptoms Score (CS), Average Combined Symptoms Score (ACS), Average Adjusted Symptoms Score (AASS or AdSS)) (See Clark J. et al., Allergy 2007: 62: 1023-1028; Pfaar et al., Allergy 2014: 69: 854-867), ACT (Asthma Symptoms Score), ACQ (Asthma Control Questionnaire), GINA asthma management guide (Global Initiative for Asthma).

Patient

The patient is preferably a mammal, such as a rodent, a feline, an equine, a bovine, an ovine, a canine or a primate, and is preferably a human, in particular a child, a woman, a man.

The "allergic patient" includes any individual allergic to the allergen who is a candidate for allergen immunotherapy. For allergen immunotherapy, in most cases, the patient is an individual who has, or has had at any time in the past, clinical symptoms of allergy and/or sensitization to an allergen and/or an allergen-specific IgE response, or an individual at risk of developing such symptoms. Sensitisation to an allergen may be assessed by detecting IgE directed against allergen(s) from this source in the serum of the patient or by skin testing with a preparation containing the corresponding allergen(s).

T-Cell Reactivity

The method for classifying an allergic patient as eligible to allergen immunotherapy comprises screening the T cell reactivity of said patient to an allergen.

Screening T cell reactivity to an allergen comprises contacting with the allergen an isolated biological sample of the patient containing T cells (typically the patient's sample consists of peripheral blood mononuclear cells (PBMCs), or less commonly of blood or a diluted blood sample), and measuring T cell reactivity to said allergen.

Measuring T cell reactivity to an allergen typically comprises measuring the proliferative response of allergen-specific T cells of the patient to stimulation with the allergen, a measure also called T cell proliferation assay.

Typically, measuring T cell reactivity is performed by a method which comprises culturing an isolated biological sample of the patient containing T cells in a culture medium comprising the allergen, for instance for at least 16 h (e.g. for about 24 h, or 48 h), and measuring the proliferative response of allergen-specific T cells of the patient to stimulation with the allergen.

Said method generally further comprises culturing the isolated biological sample of the patient containing T cells in the culture medium in absence of the allergen (i.e. negative control, "T cells unstimulated by the allergen"), for the same period of time and under the same culture conditions. Hence, in step c), T cell reactivity of the isolated biological sample of the patient containing T cells unstimulated by the allergen is measured after culturing the isolated biological sample of the patient containing T cells in the culture medium in absence of the allergen.

Said method may further comprise culturing the isolated biological sample of the patient containing T cells in the culture medium in the presence of IL-2 (typically 2 U of IL-2) as a positive control, as Il-2 promotes T cell proliferation. The use of a positive control makes it possible to verify that the T cell proliferation assay was implemented in conditions allowing for T cell proliferation.

Measuring T cell proliferation preferably comprises measuring proliferation of allergen-specific T $CD4^+$ cells, still preferably of Th2 cells. The Th2 profile of T CD4+ cells can be determined by identifying cytokines secreted by the activated cells, as Th2 cells secrete IL-4, IL-5, IL-9, IL-13, and IL-17E/IL-25. According to an embodiment, measuring T cell reactivity comprises measuring the number of T cells secreting IL-4 and/or IL-13.

A method to detect T cell proliferation in response to allergen stimulation comprises the addition of a radioactive nucleoside, such as 3H-thymidine, to a culture comprising T cells of the patient and the allergen, which radioactive nucleoside is automatically incorporated into new strands of chromosomal DNA during mitotic cell division. Subsequently, T cell proliferation is assessed by measuring the radioactivity in DNA recovered from the cell sample using a scintillation beta-counter.

As an alternative to radioactivity, T cell proliferation is measured using fluorescent dye(s) (such as carboxyfluorescein N-succinimidyl ester, CFSE) and flow cytometry. One common approach is the staining of cells with a special fluorescent dye, which is then diluted through each cell division. This decrease in the concentration of the dye is measured by flow cytometry and is inversely correlated to cell proliferation.

According to another embodiment, T cell proliferation is measured by staining stimulated cells with antibodies targeting markers associated with proliferation, such as Ki67 or CD69.

A (relative) stimulation index is calculated as the ratio of the T cell reactivity to the allergen on the T cell reactivity of the isolated biological sample of the patient containing T cells unstimulated by the allergen (T cells contacted with culture medium in absence of the allergen). According to an embodiment the stimulation index is calculated based on proliferation of allergen-specific T $CD4^+$ cells, still preferably proliferation of allergen-specific Th2 cells.

Measuring patient's T cell reactivity to the allergen may be implemented before initiation of allergen immunotherapy. Measuring patient's T cell reactivity to the allergen may be implemented in the course of an allergen immunotherapy already initiated, in particular, when the patient is to take another batch of allergen composition, e.g. allergen extract, in order to make it possible to address potential batch to batch variation in the allergens of the allergen composition used for allergen immunotherapy.

Cytokine secretion can be typically assessed by an ELISPOT which provides measurement of cytokine-secreting cells at the single cell level. For the ELISPOT assay, antibodies for the target cytokine(s) are coated for instance onto a microplate, and the sample containing T cells that is being assessed is cultured in the same wells, stimulated with the allergen to release cytokines, and then the cells are removed. Bound cytokines are visualized as with an ELISA, using detectably labelled antibodies specific for the cytokine to be detected, with each spot corresponding to a single cell secreting the cytokine.

Classification of Patients as Eligible or Non Eligible to Treatment with a Composition Comprising Said Allergen The allergen-specific T cell reactivity of the patient is compared with the patient's T cell reactivity in absence of the allergen, by calculating a stimulation index, as explained above.

In the method classifying for classifying an allergic patient, said patient is classified as being eligible to treatment with a composition comprising said allergen if stimulation index is equal or above a threshold value.

In the method classifying for classifying an allergic patient, if the calculated stimulation index is below the threshold value, the allergic patient is classified as not eligible to treatment with a composition comprising said allergen.

According to an embodiment, the threshold value is at least 10, and preferably the threshold value is 15, 20, 25, 30, 35, 40 or 50.

Method of Treatment

According to an embodiment, the method for classifying a patient as eligible to allergen immunotherapy further comprises administering to the patient a composition comprising the allergen if the patient is classified as eligible to allergen immunotherapy.

The invention further relates to a method of treating a patient allergic to an allergen, which comprises classifying if the patient is eligible to allergen immunotherapy by implementing the method for classifying a patient according to the invention, and administering to the patient a composition comprising the allergen if the patient is identified as eligible to allergen immunotherapy.

Accordingly the invention also relates to an allergen for use in a method of allergen immunotherapy, wherein said method comprises identifying if an allergic patient is eligible to treatment with a composition comprising the allergen by a method of the invention, and administering to the patient a composition comprising the allergen if the patient is identified as eligible to treatment with said composition comprising the allergen.

When the patient is classified as not eligible to the allergen immunotherapy, the patient may further be submitted to Component resolved diagnosis (CRD) to determine the patient's specific IgE concentration against individual allergenic proteins of the allergen comprised in the composition used for allergen immunotherapy (e.g. allergen extract). The allergen to be used for allergen immunotherapy is then spiked with the allergenic protein(s) to which the patient is sensitized, as identified by the Component resolved diagnosis. The spiking may be done using recombinant allergenic protein(s) or highly purified allergenic protein(s) from an allergen extract (e.g. >75%, or >85% pure allergenic protein).

Thus, according to another embodiment, the method for classifying a patient as eligible to allergen immunotherapy further comprises, if the patient is classified as not eligible to allergen immunotherapy:

e) Determining the patient's sensitivity to individual allergenic proteins of the allergen;

f) Spiking the allergen with the allergenic protein(s) to which the patient is sensitized; and g) Administering to the patient the spiked allergen.

Accordingly, the invention further relates to a spiked allergen for use in a method of allergen immunotherapy, wherein said method comprises classifying an allergic patient as not eligible to treatment with a composition comprising the allergen by a method of the invention, determining the patient's sensitivity to individual allergenic proteins of the allergen, spiking the allergen with the allergenic protein(s) to which the patient is sensitized, and administering to the patient a composition comprising the spiked allergen.

The invention will be further illustrated by the following FIGURE and examples.

DESCRIPTION OF THE PREFERRED EMBODIMENTS

Example 1: T Cell Proliferation Assay

T cell proliferation assays is performed as described in Tscheppe et al. J Allergy Clin Immunol 2020; 145:229-38.

PBMCs are isolated from the blood of allergic patients and cultivated with 1 to 10 μg/mL of the allergen. Proliferation is measured through incorporation of tritiated thymidine within 16 hours. Results are expressed as stimulation indices (SIs), which is calculated as the ratio of the amounts of radioactivity in allergen-stimulated PBMCs and unstimulated cells.

For confirming allergen-specific proliferation of T $CD4^+$ cells, carboxyfluorescein N-succinimidyl ester (CFSE) staining is performed, and expression of cell-surface markers is measured by using flow cytometry. In details, freshly isolated PBMCs of patient are cultivated in the presence of CFSE with 6 μg/mL of the allergen. As positive and negative controls 2 U of IL-2 and medium are used. On day eight, PBMCs are restimulated with phorbol 12-myristate 13-acetate and ionomycin. Following 2 hours of stimulation, PBMCs are treated with brefeldin A for 5 hours and subsequently stained with Viability Dye 780. After fixing, cells are stained with anti-human CD8 antibody and anti-human CD3 antibody. Viable lymphocytes are gated for $CD3^+$, $CD8^-$ and $CFSE^{low}$. The percentage of proliferating (carboxyfluorescein N-succinimidyl ester-low) cells among $CD4^+$ T cells ($CD3^+CD8^-$ cells) is thereby evaluated.

Example 2: ELISPOT for Assaying IL-4 and/or IL-13 Secretion

The production of IL-4 and/or IL-13 by PBMCs post-stimulation with the allergen in analyzed in dual ELISPOT assays. Flat-bottom 96-well nitrocellulose plates are coated with either 10 μg/ml of both anti-human IL-4 and anti-human IL-13. PBMC are then incubated at a density of $1\times10^5$/well either with 1 to 10 μg/ml of the allergen (either allergenic peptide pools or allergen extract), or control medium. After 24 h, cells are removed, and plates are incubated with a cocktail containing biotinylated anti-human IL-4 and horseradish peroxidase (HRP)-conjugated anti-human IL-13 at 37° C. After 2 h, spots corresponding to the biotinylated IL-4 Ab are developed by incubation with Alkaline-phosphatase-Complex (Vector Laboratories, Burlingame, CA) and then visualized by applying the Vector Blue Alkaline Phosphatase Substrate Kit III (Vector Laboratories, Burlingame, CA) according to the manufacturer's instructions. Spots corresponding to the HRP-conjugated anti-human IL-13 Ab are visualized by incubation with 3-amino-9-ethylcarvazole solution (Sigma-Aldrich, St. Louis, MO). Spots are counted by computer-assisted image analysis (KS-ELISPOT reader, Zeiss, Munich). Each assay is performed in triplicate. The level of statistical significance is determined with a Student t test using the mean of triplicate values of the response against the allergen versus the response against the control. Criteria for response positivity were 20 spot-forming cells (SFCs)/$10^6$ PBMC, $p<0.05$, and a stimulation index (SI)·2. SFCs are measured per $10^5$ PBMC, subsequently readings are background subtracted and multiplied by 10 to be expressed as SFC per million PBMC.

The invention claimed is:

1. A method of treating a patient allergic to an antigen comprising:

(i) classifying said allergic patient as eligible to allergen immunotherapy, said method comprising screening the T cell reactivity of said patient to an allergen, said screening comprising the following steps:

a) contacting with an allergen an isolated biological sample of the patient containing T cells, b) measuring T cell reactivity to said allergen, c) calculating a stimulation index as the ratio of the T cell reactivity measured in step b) on T cell reactivity of the isolated biological sample of the patient containing T cells unstimulated by the allergen, d) classifying said patient as being eligible to treatment with a composition comprising said allergen if the stimulation index is equal or above a threshold value; and (iia) administering to the patient a composition comprising the allergen if the patient is classified as being eligible to treatment with a composition comprising said allergen, and (iib) if the patient is not classified as eligible to treatment with a composition comprising said allergen:

a) determining the patient's sensitivity to individual allergenic proteins of the allergen;

b) spiking the allergen with the allergenic protein(s) to which the patient is sensitized; and c) administering to the patient the spiked allergen.

2. The method of claim 1, wherein the threshold value is at least 10.

3. The method of claim 1, wherein measuring T cell reactivity comprises measuring the proliferative response of T cells of the patient specific for the allergen.

4. The method of claim 1, wherein measuring T cell reactivity comprises measuring the number of T cells secreting one or more cytokine(s) selected from the group consisting of IL-4, IL-5, IL-9, IL-13, and IL-17E/IL-25.

5. The method of claim 4, wherein measuring T cell reactivity comprises measuring the number of T cells secreting IL-4 and/or IL-13.

6. The method of claim 1, wherein step a) comprises culturing peripheral blood mononuclear cells (PBMCs) of the patient with the allergen.

7. The method of claim 1, wherein, in step c), T cell reactivity of the isolated biological sample of the patient containing T cells unstimulated by the allergen is measured after culturing the isolated biological sample of the patient containing T cells in a culture medium in absence of the allergen.

8. The method according to claim 1, wherein the allergen comprises or consist of an allergen extract or a mixture of allergenic peptides.

9. The method according to claim 1, wherein the allergen is from a source of allergens to which the patient is allergic.

10. The method according to claim 1, wherein the allergen comprises an allergen from pollen, tree pollen, herb pollen, weed pollen, grass pollen, food, a house dust mite, or an animal or insect.

11. The method of claim 2, wherein measuring T cell reactivity comprises measuring the proliferative response of T cells of the patient specific for the allergen.

12. The method of claim 2, wherein measuring T cell reactivity comprises measuring the number of T cells secreting one or more cytokine(s) selected from the group consisting of IL-4, IL-5, IL-9, IL-13, and IL-17E/IL-25.

13. The method of claim 3, wherein measuring T cell reactivity comprises measuring the number of T cells secreting one or more cytokine(s) selected from the group consisting of IL-4, IL-5, IL-9, IL-13, and IL-17E/IL-25.

14. The method of claim 2, wherein step a) comprises culturing peripheral blood mononuclear cells (PBMCs) of the patient with the allergen.

15. The method of claim 3, wherein step a) comprises culturing peripheral blood mononuclear cells (PBMCs) of the patient with the allergen.

16. The method of claim 4, wherein step a) comprises culturing peripheral blood mononuclear cells (PBMCs) of the patient with the allergen.

17. The method of claim 5, wherein step a) comprises culturing peripheral blood mononuclear cells (PBMCs) of the patient with the allergen.

18. The method of claim 2, wherein, in step c), T cell reactivity of the isolated biological sample of the patient containing T cells unstimulated by the allergen is measured after culturing the isolated biological sample of the patient containing T cells in a culture medium in absence of the allergen.

* * * * *